US009855315B2

(12) United States Patent
Park et al.

(10) Patent No.: US 9,855,315 B2
(45) Date of Patent: Jan. 2, 2018

(54) PHARMACEUTICAL COMPOSITION COMPRISING CCN5 FOR REDUCING CARDIAC FIBROSIS IN A SUBJECT IN NEED THEREOF

(75) Inventors: Woo Jin Park, Seoul (KR); Pyoung Oh Yoon, Gwangju (KR); Dong Kwon Yang, Gwangju (KR)

(73) Assignee: BETHPHAGEN INC., Buk-Gu, Gwangju (KR)

( * ) Notice: Subject to any disclaimer, the term of this patent is extended or adjusted under 35 U.S.C. 154(b) by 782 days.

(21) Appl. No.: 13/636,500

(22) PCT Filed: Mar. 10, 2011

(86) PCT No.: PCT/KR2011/001685
§ 371 (c)(1),
(2), (4) Date: Sep. 12, 2013

(87) PCT Pub. No.: WO2011/118928
PCT Pub. Date: Sep. 29, 2011

(65) Prior Publication Data
US 2013/0345130 A1    Dec. 26, 2013

(30) Foreign Application Priority Data

Mar. 22, 2010   (KR) ........................ 10-2010-0025109

(51) Int. Cl.
*A61K 48/00*     (2006.01)
*A61K 38/18*     (2006.01)
*C07K 14/475*    (2006.01)
*G01N 33/68*     (2006.01)
*A61K 31/7088*   (2006.01)
*A61K 38/17*     (2006.01)
*A01K 67/027*    (2006.01)

(52) U.S. Cl.
CPC .......... *A61K 38/18* (2013.01); *A61K 31/7088* (2013.01); *A61K 38/179* (2013.01); *C07K 14/475* (2013.01); *G01N 33/6893* (2013.01); *A01K 67/0275* (2013.01); *C12N 2799/022* (2013.01); *G01N 2800/325* (2013.01)

(58) Field of Classification Search
CPC .... A01K 67/027; A61K 38/18; A61K 38/179; A61K 31/7088; C07K 14/475; C12N 2799/022; G01N 2800/325; G01N 33/6893

See application file for complete search history.

(56) References Cited

U.S. PATENT DOCUMENTS

| | | |
|---|---|---|
| 2004/0002124 A1 | 1/2004 | Lau et al. |
| 2004/0049017 A1 | 3/2004 | Upton et al. |
| 2008/0207489 A1* | 8/2008 | Castellot et al. .................. 514/2 |
| 2011/0275563 A1* | 11/2011 | Attramadal et al. ........... 514/7.6 |

FOREIGN PATENT DOCUMENTS

EP    1 382 347 A1    1/2004

OTHER PUBLICATIONS

Orkin et al. Report and Recommendations of the panel to assess the NIH investement in research on gene therapy. National Institutes of Health Report, Dec. 7, 1995.*
Fishbein et al. "Site-specific gene therapy for cardiovascular disease."Curr Opin Drug Discov Devel. Mar. 2010;13(2):203-13.*
Vassalli et al. "Modalities and future prospects of gene therapy in heart transplantation."Eur J Cardiothorac Surg. Jun. 2009;35(6):1036-44.*
Burghoff et al. "Horizontal gene transfer from human endothelial cells to rat cardiomyocytes after intracoronary transplantation." Cardiovasc Res. Feb. 1, 2008;77(3):534-43.*
Raake et al. "Gene therapy targets in heart failure: the path to translation." Clin Pharmacol Ther. Oct. 2011;90(4):542-53.*
Pleger et al. "Cardiac AAV9-S100A1 gene therapy rescues postischemic heart failure in a preclinical large animal model."Sci Transl Med. Jul. 20, 2011;3(92):92ra64.*
Han et al. "Remission of Diabetes by Insulin Gene Therapy Using a Hepatocyte-specific and Glucose-responsive Synthetic Promoter"Molecular Therapy (2011) 19 3, 470-478.*

* cited by examiner

*Primary Examiner* — Titilayo Moloye
(74) *Attorney, Agent, or Firm* — Harness, Dickey & Pierce, P.L.C.

(57) ABSTRACT

The present invention relates to a pharmaceutical composition for preventing or treating a heart failure and a method for screening a therapeutic agent for preventing or treating a heart failure. The pharmaceutical composition of the present disclosure comprises the CCN5 or CCN2ΔCT protein, or a genetic carrier comprising a nucleotide sequence encoding the CCN5 or the CCN2ΔCT protein, exhibiting dramatic prevention or treatment efficacies on a heart failure even without surgical treatments accompanied with transplanting a donor heart.

4 Claims, 6 Drawing Sheets

PHARMACEUTICAL COMPOSITION COMPRISING CCN5 FOR REDUCING CARDIAC FIBROSIS IN A SUBJECT IN NEED THEREOF

This is a National Phase Application filed under 35 U.S.C. 371 as a national stage of PCT/KR2011/001685, filed on 10 Mar. 2011, an application claiming the benefit from Korean Application No. 10-2010-0025109, filed on Mar. 22, 2010, the entire content of each of which is hereby incorporated by reference in its entirety.

BACKGROUND OF THE INVENTION

Field of the Invention

The present disclosure relates to pharmaceutical composition and method for screening a therapeutic agent for preventing or treating heart failure.

The Sequence Listing submitted in text format (.txt) filed on Sep. 21, 2012, named "Rev Sequence Lising.txt", (created on Sep. 21, 2012, 7 KB), is incorporated herein by reference.

Description of the Related Art

A heart disease is considered as one of the most prevalent adult diseases along with diabetes and hypertension. The heart disease is responsible for 17 million annual deaths over worldwide, and causes about 2,600 daily deaths in the United States which is one of the most serious countries for heart diseases. Therefore, the development of heart disease-related medications and treatments is actively being made in advanced countries, and the global market size reaches about 45 billion dollars. Under the recognition of importance for heart diseases, lots of studies have been undergone in Korea.

As the heart is subject to the blood pressure overload due to several pathogenic factors such as obesity, diabetes, and hypertension, it shows myocardial hypertrophy. The cell proliferation no longer occurs in the heart because the embryological differentiation of the heart is completely terminated. Therefore, it is the only way to strengthen the cardiac contractility that increases the size of the existing cardiac muscle cells, when strengthening the cardiac output is needed. This physiological phenomenon is called myocardial hypertrophy.

The cardiac muscle known as cardiomyocytes or cardiac myocytes is one of striated muscles found in a heart wall. The cardiac muscle is similar to the skeletal muscle in the senses that both of them have striated pattern and contractility, but fundamentally different from the smooth muscle in terms of structure, function and stimulus-contraction response.

The myocardial hypertrophy is considered as the compensation response for external stimuli but itself is not a serious problem. However, the myocardial hypertrophy may be exacerbated to the heart failure when it keeps last for a long period of time [1-3]. The heart failure is characterized by a defective heart function by a thinner heart wall by apoptosis and an extended lumen of the atrium and ventricle. In human, the myocardial hypertrophy (more accurately, LVH: left ventricular hypertrophy) occurs by various etiological causes and the myocardial infarction occurs by the coronary artery obstruction. They induce the diastolic and systolic dysfunction, respectively, and may be maintained without specific symptoms for several years or decades depending on persons. If the myocardial hypertrophy and the myocardial infarction are developed to the heart failure, the sudden death is very likely to occur in several months or years. Although the myocardial hypertrophy per se is not considered as a serious problem, it is classified as a risk factor which may result in the sudden death because of its higher progression probability to the heart failure.

A group of matricellular proteins known as the CCN (Cyr61, CTGF, and Nov) family has recently been described [5]. These are secreted, cell- and matrix-associated proteins with diverse roles in various aspects of cell function, including wound repair, vascular disease, fibrosis, angiogenesis, tumorigenesis, cell differentiation and survival [6]. Previous studies have indicated that CCN2, also known as CTGF (Connective Tissue Growth Factor), plays a role in the development of cardiac fibrosis. The expression of CCN2 was induced by TGF-β, a pro-fibrotic cytokine, in cardiac fibroblasts and cardiomyocytes [7]. CCN2 was shown to be an essential mediator of the physiological effects of TGF-β [8]. CCN2 has also been implicated in cardiac hypertrophy [9]. The expression of CCN2 has been reported to be elevated in the hypertrophied and failing hearts [9-11]. Treatment with CCN2 in isolated cardiomyocytes caused an Akt signaling-mediated increase in cell size [12]. Transgene-mediated overexpression of CCN2 in the mouse heart promoted the age-dependent development of cardiac hypertrophy, but did not induce cardiac fibrosis [13].

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THIS INVENTION

The present inventors have made intensive efforts to develop a pharmaceutical composition for preventing or treating a heart failure even with no surgical treatment of transplanting a donor heart. As a result, they have found out that the CCN5 protein and CCN2□CT protein have anti-hypertrophic effects which effectively inhibit the hypertrophy of the heart wall.

It is one object of this invention to provide a pharmaceutical composition for preventing or treating a heart failure.

It is another object of this invention to provide a method for screening a therapeutic agent for preventing or treating a heart failure.

Other objects and advantages of the present invention will become apparent from the following detailed description together with the appended claims and drawings.

In one aspect of this invention, there is provide a pharmaceutical composition for preventing or treating a heart failure, comprising (a) a pharmaceutically effective amount of a genetic carrier comprising (i) a nucleotide sequence encoding the CCN (Cyr61, CTGF, and Nov)5 protein or (ii) a nucleotide sequence encoding the CCN2ΔCT protein with deleted CT domain from the CCN2 protein; and (b) a pharmaceutically acceptable carrier.

The CCN5 protein is a matricellular protein belonging to the CCN family protein [5]. Little is known about functional roles of the CCN5 protein in cardiac tissue unlike other CCN family proteins. The CCN5 protein inhibits proliferation and mobility of cells in nonstriated muscles [15, 17-19]. Such effects of the CCN5 protein are shown contrary to effects of the CCN1 protein and CCN2 protein to promote proliferation and mobility of cells [20, 21].

The CCN1-4 protein and CCN6 protein contain distinguishable 4 domains as follows: (i) insulin-like growth factor binding domain, (ii) von Willebrand factor type-C, (iii) thrombospondin type-1 and (iv) C-terminal domain [22]. However, the CCN5 protein lacks the CT domain which allows the CCN1 protein and CCN2 protein for cell proliferation activity [23]. Given its structural differences, it may be assumed with no robust evidence that the CCN5 protein has different functions from other CCN family proteins.

Beyond such assumption, the present inventors have carried out specific researches and experiments and then elucidated that the CCN5 protein has anti-hypertrophic effects in myocardial hypertrophy with increased size of myocardial cells and the CCN2 protein has pro-hypertrophic effects. Especially, we have found that the CCN5 protein prevents myocardial hypertrophy by inhibiting the TGF-β-SMAD signal pathway.

The inventors of the present disclosure have elucidated that the CCN2ΔCT protein with deleted CT domain from the CCN2 protein as a pro-hypotrophic factor has anti-hypotrophic effects. The CT domain structure described above is similar to the structure found in various growth factors including VEGF, TGF-13, BMP, NGF and PDGF [31, 32]. The CT domain structure contains a cysteine knot motif with six conserved cysteine residues considered to play a role as a dimerization module.

According to a preferable embodiment, a nucleotide sequence encoding the CCN5 protein comprises the nucleotide sequence described in SEQ ID NO:1.

According to another preferable embodiment, a nucleotide sequence encoding the CCN2ΔCT protein with deleted CT domain from the CCN2 protein comprises the nucleotide sequence described in SEQ ID NO:2.

The pharmaceutical composition of the present invention prevents or treats a heart failure by inhibiting the TGF-β-SMAD signal pathway which induces a heart failure.

The term "gene delivery" as used herein, refers to transport exogenous nucleic acid molecules to a target cell or tissue. As used herein, "delivery" is used interchangeably with "transduction". At the level of tissue, the term "delivery" is used interchangeably with "spread". Therefore, the term "gene delivery system" may also be written as "gene transduction system" or "gene spread system".

To construct the present gene delivery system, it is preferred that the nucleotide sequence encoding the CCN5 protein or CCN2ΔCT protein is contained in a suitable expression construct. According the expression construct, it is preferred that the nucleotide sequence encoding the CCN5 protein or CCN2ΔCT protein is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. According to the present invention, the promoter linked to the nucleotide sequence encoding the CCN5 protein or CCN2ΔCT protein is operable in, preferably, animal, more preferably, mammalian cells, to control transcription of the chimeric decoy receptor gene, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter, but is not limited to. Most preferably, the promoter is CMV promoter.

The genetic carrier of the present invention may be manufactured in various forms including a naked recombinant DNA molecule, a plasmid, a virus vector and the liposome or niosome encapsulating the naked recombinant DNA molecule or the plasmid.

The nucleotide sequence encoding the CCN5 protein or CCN2ΔCT protein of the present invention comprises any of gene delivery system used in gene therapy by those skilled in the art, preferably, plasmid, adenovirus (Lockett L J, et al., Clin. Cancer Res., 3:2075-2080 (1997)), adeno-associated virus (AAV, Lashford L S., et al., Gene Therapy Technologies, Applications and Regulations Ed, A, Meager, 1999), retrovirus (Gunzburg W H, et al., Retroviral vectors. Gene Therapy Technologies, Applications and Regulations Ed. A. Meager, 1999), lentivirus (Wang G. et al., J. Clin. Invest. 104(11):R55-62 (1999)), herpes simplex virus (Chamber R., et al., Proc. Natl. Acad. Sci USA, 92:1411-1415 (1995)), vaccinia virus (Puhlmann M. et al., Human Gene Therapy, 10:649-657 (1999)) liposome ((Methods in Molecular Biology, Vol 199, S. C. Basu and M. Basu (Eds.), Human Press 2002)) or niosome. Most preferably, the gene delivery system of this invention is constructed by incorporating the nucleotide sequence encoding the CCN5 protein or CCN2ΔCT protein to adenovirus.

i. Adenovirus

Adenoviruses have been usually employed as a gene delivery system because of its mid-sized genome, ease of manipulation, high titer, wide target-cell range, and high infectivity. Both ends of the viral genome contains 100-200 bp ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., Cell, 31:543-551 (1982); and Riordan, J. R. et al., Science, 245:1066-1073 (1989)). Therefore, it is preferred that the nucleotide sequence encoding the CCN5 protein or CCN2ΔCT protein of this invention is inserted into either the deleted E1 region (E1A region and/or E1B region, preferably, E1B region) or the deleted E3 region, more preferably, the deleted E3 region. The nucleotide sequence of interest to be delivered is preferably inserted into either the deleted E1 region (E1A region and/or E1B region, preferably, E1B region) or the deleted E3 region, more preferably, the deleted E1 region. Furthermore, the inserted sequences may be incorporated into the deleted E4 region. The term used herein "deletion" with reference to viral genome encompasses whole deletion and partial deletion as well.

According to the most preferred embodiment of the present invention, the adenovirus gene transduction system of the present invention comprises "promoter-the target nucleotide sequence-poly A sequence" and "promoter-the nucleotide sequence encoding the CCN5 protein or CCN2ΔCT protein-poly A sequence". The "promoter-the target nucleotide sequence-poly A sequence" is inserted into the deleted E1 region (E1A region and/or E1B region, preferably, E1B region) or the E3 region, preferably, the deleted E1 region. The "promoter-the nucleotide sequence encoding the CCN5 protein or CCN2ΔCT protein-poly A sequence" is inserted into the deleted E1 region (E1A region and/or E1B region, preferably, E1B region) or the E3 region, preferably, the deleted E3 region. Also, the target nucleotide and the nucleotide sequence encoding the CCN5 protein or CCN2ΔCT protein may be expressed by the bicistronic expression system linked by IRES (internal ribosome entry site) like "promoter-the target nucleotide sequence-poly A sequence-IRES-the nucleotide sequence encoding the CCN5 protein or CCN2ΔCT protein-poly A sequence"

In nature, adenovirus can package approximately 105% of the wild-type genome, providing capacity for about 2 extra kb of DNA (Ghosh-Choudhury et al., *EMBO J.*, 6:1733-1739 (1987)). In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene delivery system of this invention. A great deal of biochemical and genetic information about adenovirus type 5 is known.

The foreign genes delivered by the present adenoviral gene delivery system are episomal, and therefore, have low genotoxicity to host cells. Therefore, gene therapy using the adenoviral gene delivery system of this invention may be considerably safe.

ii. Retrovirus

Retroviruses capable of carrying relatively large exogenous genes have been used as viral gene delivery vectors in the senses that they integrate their genome into a host genome and have broad host spectrum.

In order to construct a retroviral vector, the nucleotide sequence encoding the CCN5 protein or CCN2ΔCT protein and the nucleotide sequence of interest to be transferred are inserted into the viral genome in the place of certain viral sequences to produce a replication-defective virus. To produce virions, a packaging cell line containing the gag, pol and env genes but without the LTR (long terminal repeat) and ψ components is constructed (Mann et al., *Cell*, 33:153-159 (1983)). When a recombinant plasmid containing the nucleotide sequence encoding the CCN5 protein or CCN2ΔCT protein, the nucleotide sequence of interest, LTR and ψ is introduced into this cell line, the ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513 (1988)). The media containing the recombinant retroviruses is then collected, optionally concentrated and used for gene delivery.

A successful gene transfer using the second-generation retroviral vector has been reported. Kasahara et al. (*Science*, 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

iii. AAV Vector

Adeno-associated viruses are capable of infecting non-dividing cells and various types of cells, making them useful in constructing the gene delivery system of this invention. The detailed descriptions for use and preparation of MV vector are found in U.S. Pat. Nos. 5,139,941 and 4,797,368.

Research results for MV as gene delivery systems are disclosed in LaFace et al, *Viology*, 162:483486 (1988), Zhou et al., *Exp. Hematol.* (NY), 21:928-933 (1993), Walsh et al, *J. Clin. Invest.*, 94:1440-1448 (1994) and Flotte et al., *Gene Therapy*, 2:29-37 (1995). Recently, an MV vector has been approved for Phase I human trials for the treatment of cystic fibrosis.

Typically, a recombinant MV virus is made by cotransfecting a plasmid containing the gene of interest (i.e., relaxin gene and nucleotide sequence of interest to be delivered) flanked by the two MV terminal repeats (McLaughlin et al., 1988; Samulski et al., 1989) and an expression plasmid containing the wild type MV coding sequences without the terminal repeats (McCarty et al., *J. Viral.*, 65:2936-2945 (1991)).

iv. Other Viral Vectors

Other virus vectors may be used for the gene transduction system in the present invention. Vectors derived from viruses such as vaccinia virus (Puhlmann M. et al., *Human Gene Therapy* 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., *Gene*, 68:1-10 (1988)), lentivirus (Wang G. et al., *J. Clin. Invest.* 104(11):R55-62 (1999)) and herpes simplex virus (Chamber R., et al., *Proc. Natl. Acad. Sci USA* 92:1411-1415 (1995)) may be used in the present delivery systems for transferring the nucleotide sequence encoding the CCN5 protein or CCN2ΔCT protein into cells.

v. Liposome

Liposomes are formed spontaneously when phospholipids are suspended in an excess of aqueous medium. Liposome-mediated nucleic acid delivery has been very successful as described in Nicolau and Sene, *Biochim. Biophys. Acta*, 721:185-190 (1982) and Nicolau et al., *Methods Enzymol.*, 149:157-176 (1987). Example of commercially accessible reagents for transfecting animal cells using liposomes includes Lipofectamine (Gibco BRL). Liposomes entrapping the nucleotide sequence encoding the CCN5 protein or CCN2ΔCT protein and nucleotide sequence of interest interact with cells by mechanism such as endocytosis, adsorption and fusion and then transfer the sequences into cells.

Where the present gene delivery system is constructed on the basis of viral vector construction, the contacting is performed as conventional infection methods known in the art. The infection of hosts using viral vectors is well described in the above-cited publications.

Where the present gene delivery system is a naked recombinant DNA molecule or plasmid, the nucleotide sequence to be delivered are introduced into cells by microinjection (Capecchi, M. R., *Cell*, 22:479 (1980) and Harland and Weintraub, *J. Cell Biol.* 101:1094-1099 (1985)), calcium phosphate co-precipitation (Graham, F. L. et al., *Virology*, 52:456 (1973) and Chen and Okayama, *Mol. Cell. Biol* 7:2745-2752 (1987)), electroporation (Neumann, E. et al., *EMBO J.*, 1:841 (1982) and Tur-Kaspa et al., *Mol. Cell Biol.*, 6:716-718 (1986)), liposome-mediated transfection (Wong, T. K. et al., *Gene*, 10:87 (1980) and Nicolau and Sene, *Biochim. Biophys. Acta*, 721:185-190 (1982); and Nicolau et al., *Methods Enzymol.*, 149:157-176 (1987)), DEAE-dextran treatment (Gopal, *Mol. Cell Biol*, 5:1188-1190 (1985)), and particle bombardment (Yang et al., *Proc. Natl. Acad. Sci.*, 87:9568-9572 (1990)).

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate and mineral oils. The pharmaceutical composition according to the present invention may further include a lubricant, a humectant, a sweetener, a flavoring agent, an emulsifier, a suspending agent and a preservative. Details of suitable pharmaceutically acceptable carriers and formulations can be found in Remington's Pharmaceutical Sciences (19th ed., 1995).

An adequate administration amount of the pharmaceutical composition containing the genetic carrier described above of the present invention may vary depending on various factors including age, sex or disease condition of the patient, absorption rate of effective ingredients in body, elimination rate and combined drugs. The pharmaceutical composition of the present invention may be preferably administered in a daily dosage of 0.0001-100 mg/kg (body weight) of the CCN5 protein, the CCN2ΔCT protein or their gene.

The pharmaceutical composition of the present invention may be utilized in preventing or treating heart failure, myocardial hypertrophy, myocardial hypertrophy-related diseases and other diseases caused by overexpression of the TGF-β-SMAD signal pathway (such as cardiomyopathy, cardiac decompensation, various inflammations and cancer).

Either cardiac fibrosis or cardiac fibrotic disorders to be prevented or treated by the composition of the present invention may be characterized by chronic or acute disorders, and has common characteristics such as excessive collagen accumulation and defective function caused by the replacement of normal tissues by fibrous tissues. The acute cardiac fibrosis includes responses to acute hypertension, trauma, infection, surgery, burn, radiation and chemotherapeutic agents. The chronic fibrosis is caused by other chronic diseases inducing chronic hypertension, virus infection, diabetes, obesity, fatty liver and dermatosclerosis Therefore, the cardiac fibrosis to be prevented or treated by the composition of the present invention is all cardiac muscle diseases including the cardiac fibrosis caused by pathologic conditions or diseases, a radiation damage and a chemotherapeutic agent (e.g., bleomycin, chlorambucil, cyclophosphamide, methotrexate, moostin and procarbazine).

In another aspect of this invention, there is provided a pharmaceutical composition for preventing or treating a heart failure, comprising: (a) a pharmaceutically effective amount of (i) the CCN5 protein or (ii) the CCN2ΔCT protein with deleted CT domain from the CCN2 protein; and (b) a pharmaceutically acceptable carrier.

Since the CCN5 protein or CCN2ΔCT protein contained as active ingredients in the pharmaceutical composition is the protein expressed by the genetic carrier of this invention described above. Therefore, the common descriptions between them are omitted in order to avoid undue redundancy leading to the complexity of this specification.

According to a preferred embodiment, the CCN5 protein of the present invention comprises the amino acid sequence set forth in SEQ ID NO:3.

According to a preferred embodiment, the CCN2ΔCT protein of the present invention comprises the amino acid sequence set forth in SEQ ID NO:4.

The pharmaceutical composition of the present invention may be preferably administered orally or parenterally. The parenteral administration comprises intravenous, subcutaneous, intramuscular, intraperitoneal, percutaneous or local administration.

The formulation of the pharmaceutical composition may be prepared in the form of plasters, granule, powders, syrups, solutions, fluid extracts, emulsions, suspensions, infusions, tablets, injections, capsules and pills, but may be altered according to the usage.

In the composition of the present invention, in addition to the CCN5 protein or CCN2ΔCT protein itself, a pharmaceutically acceptable salt, hydrate or solvate thereof may be used as the effective ingredient.

The term "pharmaceutically acceptable salt" refers to a salt of the compound capable of producing the desired pharmacological effects, i.e. remodeling activities which not only inhibits or prevents development of myocardial hypertrophy but also restores a hypertrophic condition of the heart to normal condition. The salt is formed by using an inorganic acid (e.g., hydrochloride, hydrobromide and hydroiodide) or an organic acid (e.g., acetate, adipate, alginate, aspartate, benzoate, benzenesulfoate, p-toluenesulfoate, bisulfate, sulfamate, sulfate, naphtalate, butyrate, citrate, camphorate, camphorsulfonate, cyclopenta nepropionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate).

The term "pharmaceutically acceptable hydrate" refers to a hydrate of the CCN5 protein or CCN2ΔCT protein that produces the desired pharmacological effect. The term "pharmaceutically acceptable solvate" refers to a solvate of the CCN5 protein or CCN2ΔCT protein that produces the desired pharmacological effect. The hydrate and the solvate may also be prepared using the aforementioned acids.

An adequate administration amount of the pharmaceutical composition of the present invention may vary depending on various factors including age, sex or disease condition of the patient, absorption rate of effective ingredients in body, elimination rate and combined drugs. The pharmaceutical composition of the present invention may be preferably administered in a daily dosage of 0.0001-100 mg/kg (body weight) of either the CCN5 protein or the CCN2ΔCT protein.

In still another aspect of this invention, there is provided a method for screening a therapeutic agent for preventing or treating a heart failure, comprising: (a) contacting a test substance to cells comprising a gene encoding the CCN5 protein; and (b) analyzing the expression level of the gene encoding the CCN5 protein, when the test substance increases the expression level of the gene of CCN5 protein, it is determined as the therapeutic agent for preventing or treating the heart failure.

According to the present method, the test substance is contacted to the cells containing a gene encoding the CCN5 protein. Preferably, the cells containing the gene encoding CCN5 protein are derived from heart.

The term "test substance" used in the present screening method refers to a substance which is used in the screening to determine whether it affects expression amount of the gene encoding the CCN5 protein or an amount of CCN5 protein. The test substance screened by the present method may be chemical compounds, nucleotide, antisense-RNA, siRNA (small interference RNA) and natural extracts, but is not limited to these.

Next, the expression amount of the gene encoding the CCN5 protein or the amount of CCN5 protein in the test substance-treated cells is measured. As results, the test substance may be determined as the therapeutic agent for preventing or treating the heart failure where it increases the expression amount of the gene encoding the CCN5 protein or the amount of CCN5 protein of the present invention.

The measurement of changes in expression of a gene encoding the CCN5 protein may be carried out according to various methods known to those ordinarily skilled in the art, for example, using RT-PCR (Sambrook et al, *Molecular Cloning. A Laboratory Manual,* 3rd ed. Cold Spring Harbor Press (2001)), Northern blotting (Peter B. Kaufma et al., *Molecular and Cellular Methods in Biology and Medicine,* 102-108, CRC press), cDNA microarray hybridization (Sambrook et al, *Molecular Cloning. A Laboratory Manual,* 3rd ed. Cold Spring Harbor Press (2001)) or in situ hybridization (Sambrook et al., *Molecular Cloning. A Laboratory Manual,* 3rd ed. Cold Spring Harbor Press (2001)).

According to RT-PCR protocol, total RNA is extracted from the test substance-treated cells, and first cDNA is prepared using dT primer and reverse transcriptase. Then, PCR reaction is carried out using first cDNA as a template and a gene encoding the CCN5 protein-specific primer set. The resulting products are separated by electrophoresis and the band patterns are analyzed to measure the expression level of the gene of CCN5 protein.

In another aspect of this invention, there is provided a method of preventing or treating a heart failure, comprising administering the composition of the present invention to a subject in need thereof.

The features and advantages of this invention are summarized as follows:

(a) The present invention provides a composition for preventing or treating a heart failure and a method for screening a therapeutic agent for preventing or treating a heart failure.

(b) The pharmaceutical composition of the present disclosure comprises the CCN5 or the CCN2ΔCT protein, or a genetic carrier comprising a nucleotide sequence encoding the CCN5 or the CCN2ΔCT protein, exhibiting dramatic prevention or treatment efficacies on a heart failure even without surgical treatments accompanied with transplanting a donor heart.

BRIEF DESCRIPTION OF THE DRAWINGS

(A) Quantitative RT-PCR was performed in triplicate with 3 independent heart samples from each experimental condition (Sham, TAC 14, and TAC-R1). TAC14: 14 days after transverse aortic constriction (TAC). TAC-R1: 14 days after TAC with 1 day of constriction relief. (B) Adenoviral-mediated transfer of AdLacZ, AdCCN2, and AdCCN5 to cultured neonatal cardiomyocytes was analyzed by Western blotting. Multiplicity of infection was 100 for all infections. The putative CCN2 and CCN5 protein band was detected. (C) Sarcomeric organization of the cardiomyocytes was visualized by staining with anti-actinin antibody. Marked sarcomeric reorganization was observed in response to both PE and AdCCN2 infection. The response was completely inhibited by AdCCN5 infection. (D) The cell surface areas of the cardiomyocytes were measured using Image J software (n=50). (E) Sarcomeric reorganization of cardiomyocytes was scored semi-quantitatively on the basis of the area occupied by the reorganized sarcomere relative to the total cell area: less than ⅓ of the cell area (white bar); more than ⅓ but less than ⅔ of the cell area (gray bar); more than ⅔ of the cell area (black bar). (F and G) Cardiomyocytes were infected with AdLacZ, AdCCN2, or AdCCN2+AdCCN5 and stimulated with PE for 48 hours. Cell surface areas were measured and sarcomeric reorganization was semiquantitatively scored (n=50).

(A) Adenoviral-mediated transfer of AdLacZ, AdCCN2□CT, and AdCCN5/CT to cultured neonatal cardiomyocytes was analyzed by Western blotting. (B) Sarcomeric organization of the cardiomyocytes was visualized by staining with a nti-actinin antibody. (C) The cell surface areas of the cardiomyocytes were measured using Image J software (n=50). (D) Sarcomeric reorganization of cardiomyocytes was scored semiquantitatively as described for FIG. 1.

(A) CCN2 expression under the control of the α-MHC promoter. (B) Western blotting for CCN2 in heart extracts from wild type littermates (WT) and CCN2 TG mice (CCN2 TG line40). (C) Assessment of the heart weight/body weight (HW/BW) ratios of WT and CCN2 TG mice that had been either sham operated or constricted (TAC) for 4 weeks, (D) Cross-sections of the hearts that had undergone TAC for 4 weeks (n=6 for WT and CCN2 TG). Cross-sectional areas (CSA) were measured using the AnalySIS image analysis program (n=3 for WT and CCN2 TG), (E) Quantitative RT-PCR analysis for ANF, β-MHC and SKA transcript levels in hearts from mice that had undergone TAC for 4 weeks (n=6). *P<0.05, **p<0.01.

(A) CCN5 expression under the control of the α-MHC promoter. (B) Western blotting for CCN5 in heart extracts from wild type littermates (WT) and CCN5 TG mice (CCN5 TG line81). (C) Assessment of the heart weight/body weight (HW/BW) ratios of WT and CCN5 TG mice that had been either sham operated or constricted (TAC) for 4 weeks. (D) Cross-sections of the hearts that had undergone TAC for 4 weeks (n=6 for WT and CCN5 TG-81). Cross-sectional areas (CSA) were measured using the AnalySIS image analysis program (n=3 for WT and CCN5 TG). (E) Quantitative RTPCR analysis for ANF, β-MHC and SKA transcript levels in hearts from mice that had undergone TAC for 4 weeks (n=6). *P<0.05, **p<0.01.

(A) Trichrome staining of histological sections from heart of CCN2 and CCN5 TG mice and their corresponding WT littermates that had undergone TAC for 4 weeks. (B) Fibrotic areas were quantified using the AnalySIS image analyzer on histological sections. n=3. (C and D) Quantitative RT-PCR analysis for collagen I transcript levels (C) and TGF-β1 transcript levels (D) in hearts from mice that had undergone TAC for 4 weeks. n=3. *P<0.05, **p<0.01.

CCN2 TG and CCN5 TG mice and their corresponding WT littermates underwent TAC for 4 weeks and the resulting cardiac structure and function were monitored by echocardiography (n=8-10). LVIDS, left ventricular internal dimension at the systole; FS, fractional shortening. **p<0.01 versus baseline. □p<0.05 and p<0.01 between TG and WT littermates.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Method
Cell Culture and Hypertrophic Stimulation

Neonatal rat cardiomyocytes were obtained from 1-day-old Sprague-Dawley rats. The cardiomyocytes were isolated, cultured, and characterized as described previously [25]. Briefly, ventricular tissue was enzymatically dissociated, and the resulting cell suspension was enriched for cardiomyocytes using Percoll (Amersham Pharmacia) gradient centrifugation. Isolated cardiomyocytes were plated onto either collagencoated culture dishes (Corning) or cover slips and then cultured in medium (DMEM supplemented with 10% FBS and 2 mM L-glutamate, and 100 µM 5-bromodeoxyuridine; GIBCO BILL). To induce hypertrophy, the cardiomyocytes were cultured in serumfree medium for at least 24 hours and then treated with 100 µM phenylephrine (PE) for 24 hours.

Generation of the Recombinant Adenoviruses AdCCN2, AdCCN5, AdCCN2□CT, and AdCCN5/CT The AdEasy XL Adenoviral Vector System (Stratagene) was used to generate recombinant adenoviruses. Amino-terminal hemagglutinin (HA)-tagged full-length mouse CCN2 and CCN5 cDNAs were subcloned into the pShuttle-IRES-hrGFP2 vector. A CCN2 construct lacking the CT domain, CCN2□CT, and a CCN5 construct containing a CT domain, CCN5/CT, were generated by PCR-mediated mutagenesis and subcloned into the shuttle vector. The linearized shuttle vectors were then recombined in *Escherichia coli* strain BJ5183 (Stratagene) with a serotype 5 first-generation adenoviral backbone, AdEasy-1 (Stratagene). Successfully recombined viral backbones were transformed into AD293 cells (Stratagene) and grown in large quantities. Adenovirus was purified by standard CsCl ultracentrifugation and desalting. Viral titers were determined using the plaque assay. Cardiomyocytes were infected with the recombinant adenoviruses for 2 hours at a multiplicity of infection of 10 or 100 and incubated for an additional 48 hours to ensure transgene expression.

Generation of Transgenic Mice

Full-length mouse CCN2 and CCN5 cDNA was subcloned into pNC vector containing a 5.5-kb segment of the α-myosin heavy chain (α-MHC) promoter and human growth hormone 3' untranslated region. The DNA construct was microinjected into C57BL/6 fertilized eggs and transgenic integration was confirmed by Southern blotting (Macrogen, Korea). Transgenic mice and wild-type littermates were examined at 8 to 10 weeks of age.

Transverse Aortic Constriction (TAC)

Male mice of 8 to 10 weeks of age (25-30 g) were used. The animals were anesthetized with 0.5 ml-0.7 ml of a 1× Avertin solution (mixtures of 2-2-2 tribromoethanol and tertamyl alcohol) administered via intraperitoneal injection. The mice were ventilated with a tidal volume of 0.1 ml and a respiratory rate of 120 breaths per minute (Harvard Apparatus). A longitudinal incision of 2 to 3 mm was made in the proximal sternum to allow visualization of the aortic arch. The transverse aortic arch was ligated between the innominate and left common carotid arteries with an overlaid 27-gauge needle. The needle was then immediately removed, leaving a discrete region of constriction.

Histological Examination of Cardiac Tissues

The mice were sacrificed 4 weeks after TAC or sham operation. The heart was arrested at end-diastole and the left ventricle was freed from the right ventricle and weighed. The paraffin-embedded heart was cut into 5 µm slices and stained with hematoxylin-eosin solution. To measure the surface area of the cardiomyocytes, suitable cross-sections with nearly circular capillary profiles and nuclei were selected. These were observed using an Axiophot microscope (Carl Zeiss, Germany), and then analyzed using the Analysis-SIS3.2 software (Soft-Imaging System, Germany). To measure the fibrotic areas, trichrome staining of the sectioned hearts was performed. The fibrotic areas stained blue and the normal tissue stained red. The interstitial Fibrotic area was calculated as the ratio of the total area of interstitial fibrosis to the total area of the section.

Quantitative RT-PCR

Total RNA was isolated using TRI reagent (Sigma). Reverse transcription was performed using ImProm II reverse-transcriptase (Promega) with oligo-dT priming. PCR was performed using an ABI PRISM Sequence Detector System 7500 (Applied Biosystems) with SYBR Green (Takara) as a fluorescent dye, and ROX (Takara) as a passive reference dye. The following Rat PCR primers were used; (i) ANF, 5'-CTG CTT CGG GGG TAG GAT TG-3' and 5'-TGA CAC ACC ACA AGG GC; (ii) CCN2,5'-TAG CAA GAG CTG GGT GTG TG-3' and 5'-TTC ACT TGC CAC AAG CTG TC-3; and (iii) CCN5,5'-TTA GCA CTT GTG GTG GCT TG-3' and 5'-CCA TTG AGA GAA GGC AGA GG-3'. The following Mouse PCR primers were used; (i) ANF, 5-ACC TGC TAG ACC ACC TGG AGG AG-3' and 5'-CCT TGG CTG TTA TCT TCG GTA CCG-3'; (ii) β-MHC, 5-GAC GAG GCA GAG CAG ATC GC and 5'-GGG CTT CAC AGG CAT CCT TAG CC-3'; (iii) α-SKA, 5'-TGA GAC CAC CTA CAA CAG CA-3' and 5'-CCA GAG CTG TGA TCT CCT TC-3'; (iv) collagen 1, 5'-CGA AGG CAA CAG TCG CTT CA and 5'-GGT CTT GGT GGT TTT GTA TTC GAT; (v) TGF-β1, 5'-GTG TGG AGC AAC ATG TGG AAC TCT A-3' and 5'-TTG GTT CAG CCA CTG CCG TA-3'; (vi) GAPDH, 5'-TCC GTG TTC CTA CCC CCA ATG and 5'-GGG AGT TGC TGT TGA AGT CGC.

Echocardiography

The mice were anesthetized and their chest areas were shaved. Echocardiography was performed using a Powervision 6000 (TOSHIBA) instrument and a 12-MHz microprobe (PLM-1204AT, TOSHIBA). The heart was scanned using a short axis view and the 2-dimensional M mode.

Western Blot Analysis

Lysates were obtained by solubilizing cardiac tissue with a combination of RIPA buffer (0.1% SDS, 50 mM Tris-HCl (pH 7.4), 150 mM NaCl, 1% NP-40, 0.5% Sodium deoxycholate; Boston BioProducts), and protease inhibitor cocktail (Boehringer Mannheim, Germany). A total of 200 µg of cardiac tissue lysate was separated by SDS-PAGE and transferred to a PVDF membrane (Schleicher & Schuell, Germany). The membrane was blocked with 5% non-fat milk and incubated with antibodies against CCN2 (Abcam, USA), CCN5 (Santa Cruz, USA), phospho-Smad 2, Smad 2/3 and Smad4 (Cell Signaling, USA), Smad7 (Invitrogen, USA), and α-actinin (Cell Signaling, USA). Incubation with the primary antibody was carried out overnight in a cold room. The membrane was then incubated with a secondary antibody conjugated to horseradish peroxidase (HRP) (Jackson ImmunoResearch) and developed using a chemiluminescent substrate (PerkinElmer).

Statistics

Appropriate, data were expressed as means SDs. Group means were compared using a Student's test or a one-way ANOVA with a Bonferroni post-hoc test (Statview V5.0, SAS). P<0.05 was considered statistically significant.

Results

In Cardiomyocytes, CCN2 and CCN5 are Pro- and Anti Hypertrophic, Respectively

Figure 1:
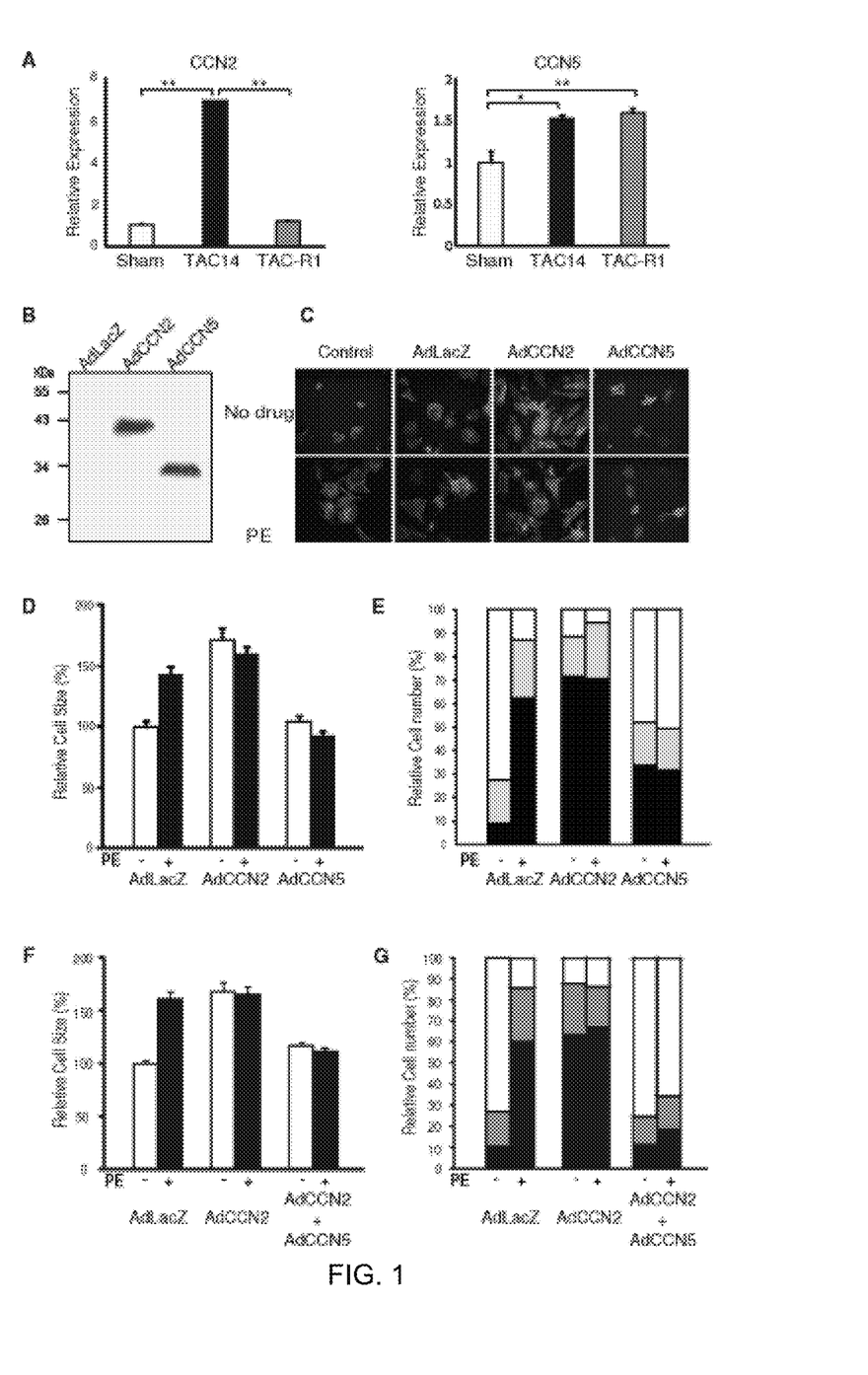
FIG. 1 shows the effects of the CCN2 protein and CCN5 protein on phenylephrine (PE)-induced hypertrophy in cultured neonatal rat cardiomyocytes.

We previously reported a model for the development and regression of cardiac hypertrophy, and isolated a number of genes that are differentially expressed during cardiac remodeling. Of these, CCN2 and CCN5 were of particular interest. Quantitative RT-PCR was performed to confirm the expression patterns that had been observed in the previous study with DNA microarray analysis (FIG. 1A). Both CCN2 and CCN5 were up-regulated under hypertrophic conditions (TAC14). However, CCN2 was sharply down-regulated during the regression period, whereas CCN5 remained elevated (TAC-R1). On the basis of these expression patterns, we hypothesized that CCN2 and CCN5 are involved in the development and the regression of cardiac hypertrophy, respectively.

To test this hypothesis, we generated recombinant adenoviruses expressing CCN2 and CCN5: AdCCN2 and AdCCN5. Western blot analyses revealed protein expression in the AdCCN2 and AdCCN5-infected cardiomyocytes but not in the noninfected or the AdLacZ-infected cardiomyocytes. The apparent molecular weights of the CCN2 and the CCN5 bands were 41 kDa and 31 kDa, respectively, which is consistent with their calculated molecular weights (FIG. 1B). At 24 hours postinfection, the cardiomyocyte cultures were stimulated with PE for 48 hours (FIG. 1C). This treatment significantly increased the size of both the non-infected and the AdLacZinfected cardiomyocytes, as assessed by measuring the surface area of the cells under a microscope. Infection with AdCCN2 significantly increased cell size in the presence or the absence of PE. In contrast, infection with AdCCN5 completely inhibited the PE-induced increase in cell size (FIG. 1D). Another feature of the hypertrophic response of cardiomyocytes is a pronounced sarcomeric rearrangement that can be detected by immunostaining with α-actinin antibody. While PE-treatment or infection with AdCCN2 significantly increased sarcomeric rearrangement, infection with AdCCN5 inhibited PE-induced sarcomeric rearrangement (FIG. 1E). When co-infected, AdCCN5 inhibited the AdCCN2-induced increase in cell size and sarcomeric rearrangement (FIGS. 1F and G). These results indicate that CCN2 and CCN5 act as a pro-hypertrophic and as an anti-hypertrophic factor, respectively, and that CCN5 acts as a dominant negative molecule against CCN2.

The CT Domain is Critical for the Hypertrophic Effect

Figure 2:
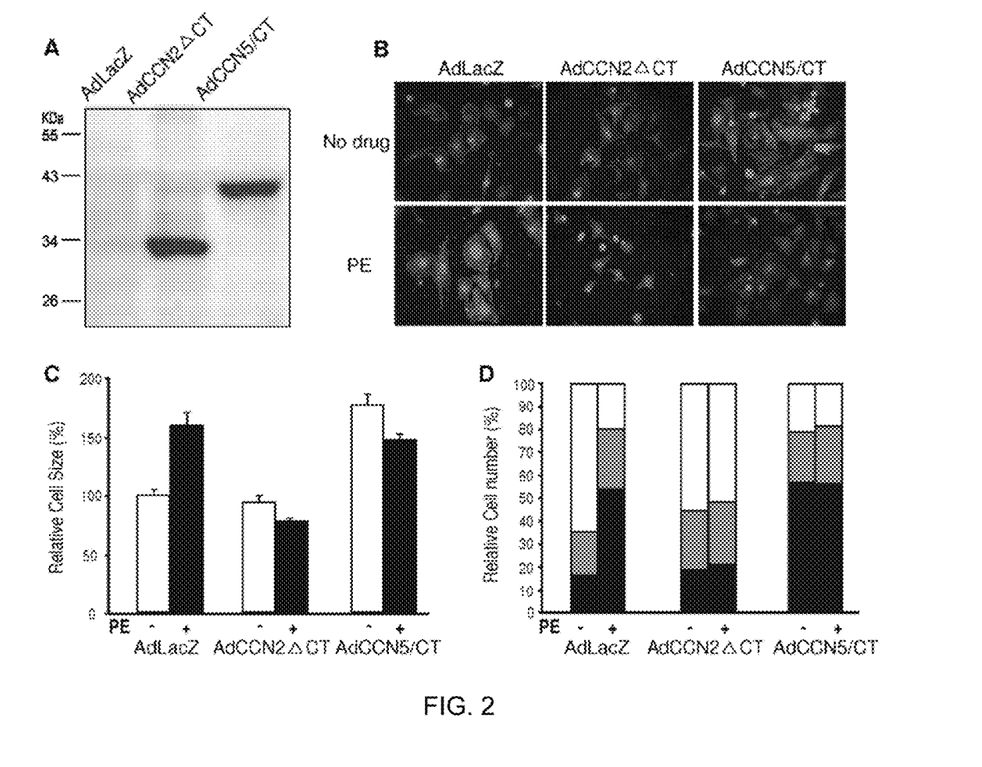
FIG. 2 represents that CCN5 is a dominant negative molecule due to lack of the CT domain.

CCN proteins contain four distinct structural domains, with the exception of CCN5 which lacks the CT domain. A previous study showed that the CT domain alone can induce hypertrophy in cardiomyocytes. To further evaluate the role of the CT domain in the function of CCN2 and CCN5, we generated two additional adenoviruses. The AdCCN2☐CT construct encodes a CCN2 protein lacking the CT domain, and the AdCCN5/CT construct encodes a CCN5 protein fused to the CT domain of CCN2. Western blot analyses revealed protein expression in the cardiomyocytes infected with AdCCN2☐CT and AdCCN5/CT (FIG. 2A). At 24 hours post-infection, the cardiomyocyte cultures were stimulated with PE for 48 hours (FIG. 2B). When assessed in terms of the increase in cell size and sarcomeric rearrangement, the effects of CCN2☐CT and CCN5/CT were indistinguishable from those of CCN5 and CCN2, respectively (FIGS. 2C and D). These results indicate that the CT domain is essential for the hypertrophic effect of CCN2, and that a CCN protein can act as a dominant negative molecule when the CT domain is deleted. These data support the hypothesis that CCN5 is a naturally occurring dominant negative molecule.

CCN2 Overexpression does not Induce Cardiac Hypertrophy In Vivo

Figure 3:
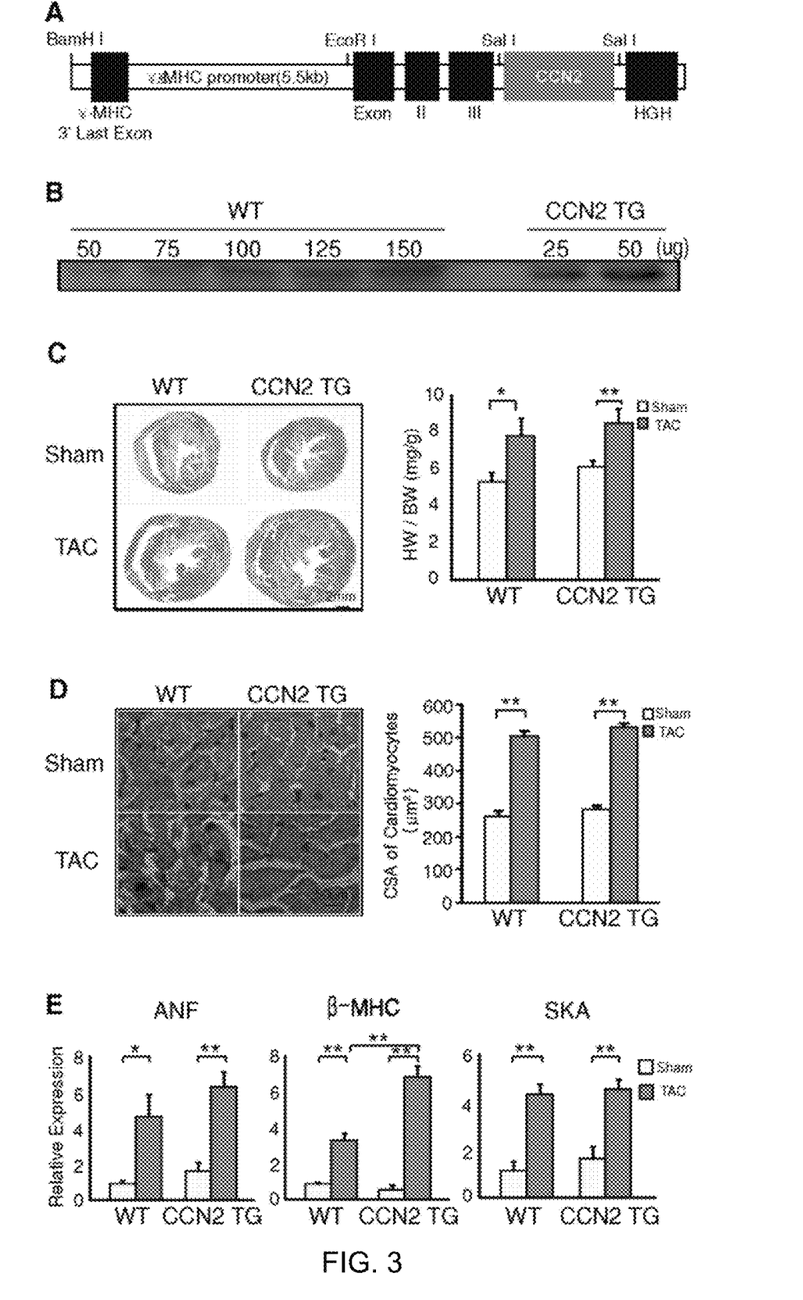
FIG. 3 represents that CCN2 does not affect cardiac hypertrophy in vivo.

To investigate the role of CCN2 in vivo, we generated transgenic (TG) mice that expressed CCN2 under the control of the α-MHC promoter (FIG. 3A). Western blot analyses revealed that cardiac CCN2 expression in the TG mice was about 4-fold higher than in wild type (WT) littermates (FIG. 3B). CCN2 TG mice and WT littermates were subjected to transverse aortic contraction (TAC) for 4 weeks, and the morphological and transcriptional changes in the heart were monitored. CCN2 TG mice developed neither cardiac hypertrophy at baseline nor enhanced hypertrophic responses to TAC, as assessed by measuring the heart weight (HW) to body weight (BW) ratio and cross-sectional areas (CSA) (FIGS. 3C and D). The induction of fetal genes (e.g., ANF, β-MHC, and skeletal-actin (SKA)) is a hall mark of cardiac hypertrophy. Quantitative RT-PCR analysis showed that no induction of these hypertrophic marker genes occurred at baseline, and that their induction was not significantly increased in response to TAC in CCN2 TG mice (FIG. 3E). One exception was ☐-MHC, for which TAC-dependent up-regulation was significantly increased in CCN2 TG mice. It is possible that other, as yet unknown, factors are required to facilitate CCN2-induced cardiac hypertrophy in vivo.

Figure 4:
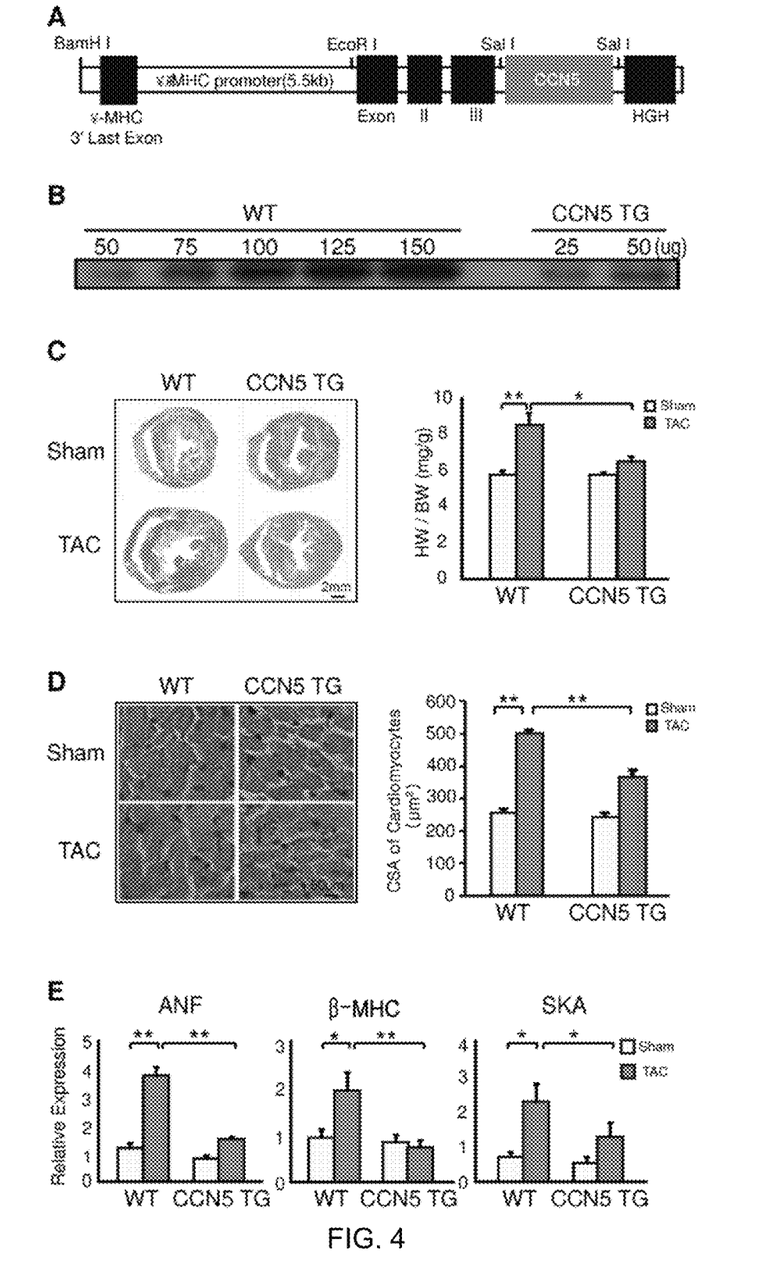
FIG. 4 represents that CCN5 inhibits cardiac hypertrophy in vivo.

CCN5 Overexpression Inhibits Pressure Overload-Induced Cardiac Hypertrophy In Vivo To investigate the role of CCN5 in vivo, we generated CCN5 TG mice (FIG. 4A). Western blot analyses revealed that cardiac CCN5 expression in the TG mice was about 2-fold higher than in WT littermates (FIG. 4B). CCN2 TG mice and WT littermates were subjected to TAC for 4 weeks. The TAC-induced cardiac hypertrophy, which was characterized by a prominent increase in the HW/BW ratio and CSA, was significantly inhibited in CCN5 TG mice (FIGS. 4 C and D). Quantitative RT-PCR analysis also showed that the induction of fetal genes by TAC was significantly inhibited in CCN5 TG mice (FIG. 4E). These results indicate that CCN5 acts as an anti-hypertrophic factor in vivo as well as in isolated cardiomyocytes.

Figure 5:
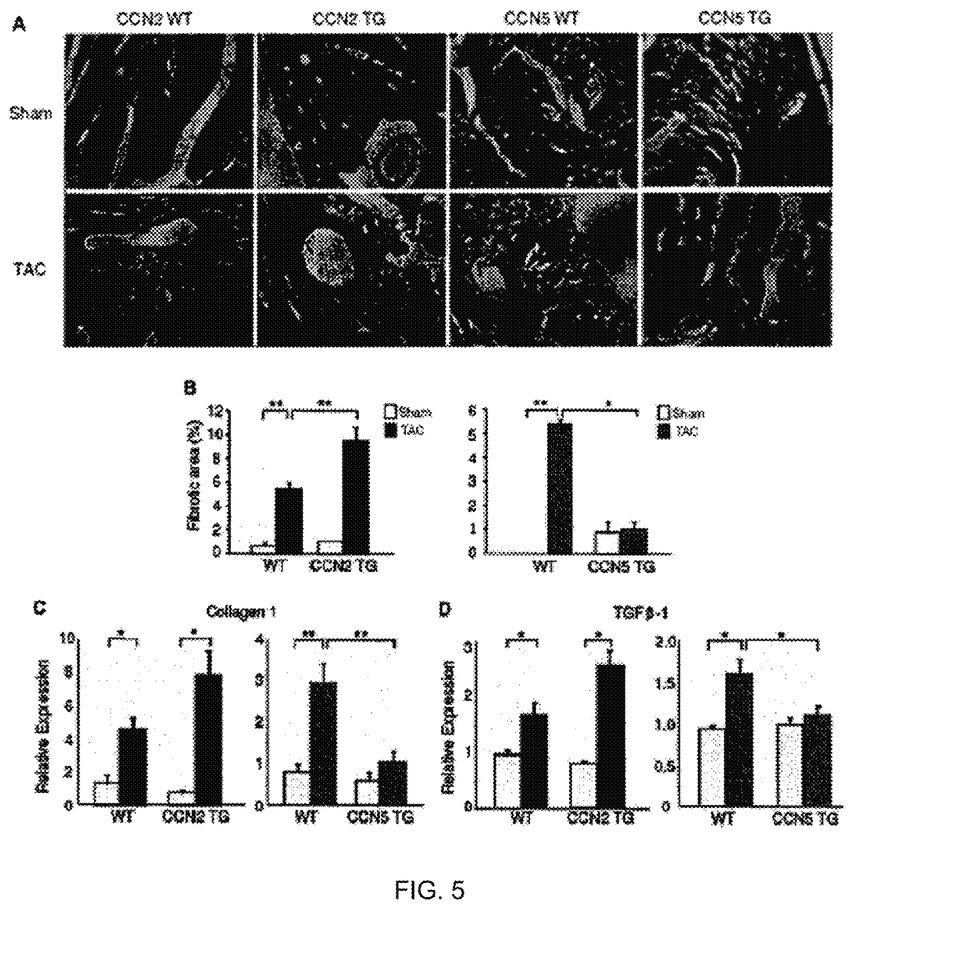
FIG. 5 represents that CCN2 accelerates cardiac fibrosis and CCN5 inhibits cardiac fibrosis in vivo.

Pressure Overload-Induced Cardiac Fibrosis is Exacerbated in CCN2 TG Mice but Inhibited in CCN5 TG Mice It has previously been reported that CCN2 is involved in TGF-β-mediated fibrosis. TG mice and WT littermates were subjected to TAC for 4 weeks, and heart sections were then examined using trichrome staining (FIG. 5A). TAC induced prominent fibrosis, as demonstrated by an increased trichrome stained-fibrotic area and an increased expression of collagen 1 and TGF-β, both of which are marker genes for fibrosis. Trichrome staining showed that this TAC-induced fibrosis was significantly exacerbated in CCN2 TG mice but significantly inhibited in CCN5 TG mice. (FIG. 5B). Quantitative RT-PCR further indicated that the up-regulation of collagen 1 and TGF-β was significantly exacerbated in CCN2 TG mice but inhibited in CCN5 TG mice (FIGS. 5C and D). These data support the hypothesis that CCN2 and CCN5 are pro-fibrotic and anti-fibrotic, respectively.

CCN5 Prevents Cardiac Decompensation in Response to Pressure Overload

Figure 6:
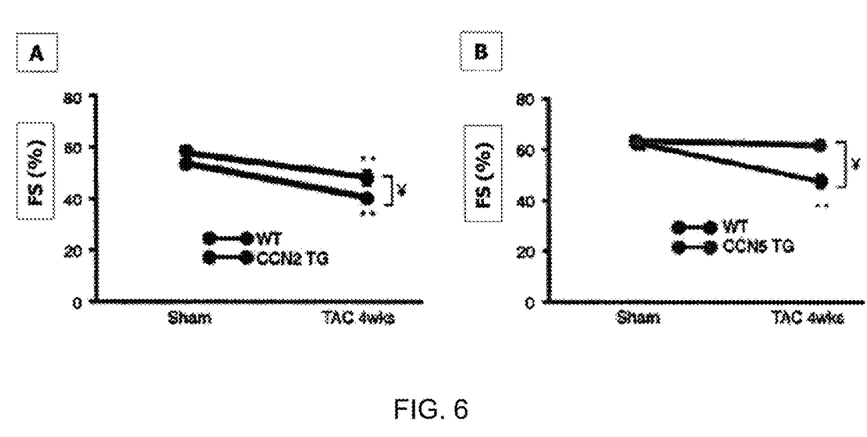
FIG. 6 represents that CCN5 prevents heart failure.

Echocardiography was performed to evaluate cardiac function following four weeks of TAC. WT littermates that had undergone the TAC procedure typically showed an 18-20% reduction in fraction shortening (FS) compared to sham-operated mice. CCN2 TG mice exhibited a 32% reduction in FS, a reduction which was significantly more pronounced than that observed in WT littermates (FIG. 6A). In contrast, no reduction in FS was observed in CCN5 TG mice under the same experimental condition (FIG. 6B). The inhibition of cardiac hypertrophy and fibrosis by CCN5 appears to prevent further cardiac deterioration in response to TAC (Table 1).

the development of significant hypertrophy. Using this model and DNA microarray gene profiling, we were able to identify a number of genes whose expression levels were altered during the development or the regression of cardiac hypertrophy [24]. In a group of genes (group 1), gene expression increased during the development of cardiac hypertrophy and decreased sharply during the regression period. In another group of genes (group 2), gene expression was upregulated and remained elevated throughout the development and regression of cardiac hypertrophy. We

TABLE 1

Echocardiographic Parameters in Sham and after AB in WT and CCN2, CCN5 TG mice

| | CCN2 WT | | CCN2 TG | | CCN5 WT | | CCN5 TG | |
|---|---|---|---|---|---|---|---|---|
| | Sham n = 8 | TAC 4 wks n = 8 | Sham n = 8 | TAC 4 wks n = 8 | Sham n = 6 | TAC 4 wks n = 10 | Sham n = 10 | TAC 4 wks n = 10 |
| BW g | 26.0 ± 2.41 | 24.7 ± 1.89 | 24.3 ± 2.51 | 24.3 ± 1.71 | 29.6 ± 2.45 | 28.6 ± 2.69 | 29.5 ± 3.42 | 27.1 ± 2.05 |
| IVSTD, mm | 0.85 ± 0.08 | 0.94 ± 0.14 | 0.78 ± 0.07 [d] | 1.04 ± 0.26 [a] | 0.83 ± 0.08 | 1.03 ± 0.13 [a] | 0.89 ± 0.10 | 0.93 ± 0.13 [d] |
| IVSTS, mm | 1.63 ± 0.17 | 1.69 ± 0.26 | 1.59 ± 0.16 | 1.68 ± 0.24 [b] | 1.67 ± 0.12 | 1.67 ± 0.23 | 1.70 ± 0.13 | 1.76 ± 0.20 |
| EF | 92.9 ± 0.83 | 84.4 ± 7.44 | 92.6 ± 1.51 | 77.5 ± 5.07 | 94.7 ± 1.21 | 80.0 ± 3.85 [a] | 94.1 ± 1.52 | 93.8 ± 2.10 [c] |
| FS % | 59.1 ± 1.46 | 48.5 ± 8.30 [a] | 59.3 ± 3.33 | 40.6 ± 4.60 [ad] | 64.2 ± 3.37 | 48.7 ± 6.59 [a] | 63.1 ± 3.57 | 62.1 ± 4.70 [c] |

[a] $P < 0.01$ vs sham
[b] $P < 0.05$ vs sham
[c] $P < 0.01$ vs NL
[d] $P < 0.05$ vs NL CCN5 Inhibits the TGF-β-SMAD Signaling Pathway Cytoplasmic protein SMADs are known to mediate intracellular TGF-3 signaling. TGF-β increases the phosphorylation of SMAD2 and SMAD3, which form heterotrimers with SMAD4. This complex translocates into the nucleus and activates the transcription of target genes. SMAD7 plays an inhibitory role in this signaling pathway. We used Western blotting to determine whether CCN2 and CCN5 affect the TGF-3-SMAD signaling pathways. Densitometry of the blots revealed that both the phosphorylation of Smad2 and the Smad4 protein levels were increased in CCN2 TG mice that had undergone TAC, but were slightly decreased in CCN5 TG mice. The level of SMAD7 was significantly reduced in CCN2 TG mice, but remained elevated in CCN5 TG mice. These data indicate that CCN2 and CCN5 modulate the TGF-β-SMAD signaling pathway.

Discussion

Cardiac hypertrophy is an independent risk factor for cardiovascular morbidity and mortality [26]. Although initially beneficial, sustained cardiac hypertrophy leads to systolic and diastolic dysfunction and ultimately the development of heart failure [27]. Intensive efforts have been made to decipher the intracellular signaling pathways that mediate cardiac hypertrophy in an attempt to design novel therapeutic strategies. Multiple signaling pathways appear to operate within the context of an orchestrated hypertrophic network. Recent studies have identified potential anti-hypertrophic and to inhibitory feedback mechanisms [28]. The augmentation of these negative regulators, as well as the inhibition of positive regulators, may provide alternative strategies for the treatment of heart failure. In the present study, we demonstrated that two members of the CCN family, CCN2 and CCN5, are pro- and anti-hypertrophic, respectively. In addition, we showed that these molecules exert opposing effects on the pressure overload-induced cardiac fibrosis.

We used a surgical model for the regression of cardiac hypertrophy, in which aortic construction was relieved after hypothesized that the genes in group 1 participate in the hypertrophic signaling pathway and that the genes in group 2 participate in counteracting hypertrophic signaling. CCN2 and CCN5 belonged to group 1 and group 2, respectively (data not shown).

In the present study, we used quantitative RT-PCR to confirm the differential expression patterns of CCN2 and CCN5 (FIG. 1A). We then investigated the effects of CCN2 and CCN5 in neonatal cardiomyocytes using recombinant adenoviruses expressing CCN2 and CCN5 (FIG. 1B-E). In accordance with our hypothesis, CCN2 induced cell growth and sarcomeric rearrangement in the presence or the absence of PE, whereas CCN5 inhibited PE-induced hypertrophic phenotypes. When its CT domain was deleted, CCN2 behaved like CCN5. When CCN5 was fused with the CT domain of CCN2, it behaved like CCN2 (FIG. 2A-D). This observation indicates that the CT domain is critical for the hypertrophic activity of CCN2, as has been reported previously [12]. When co-infected, CCN5 inhibited CCN2-induced hypertrophic phenotypes (FIGS. 2E and F), suggesting that CCN5 acts as a dominant negative molecule for CCN2. Surprisingly, CCN2 overexpression in TG mice neither induced cardiac hypertrophy at baseline nor enhanced pressure overload-induced cardiac hypertrophy (FIG. 3). Consistent with our data, it was recently shown that CCN2 promotes cardiac hypertrophy only in aged, but not in young, TG mice [13]. CCN2 significantly enhanced pressure overload-induced cardiac fibrosis (FIG. 5). It is possible that other, as yet unknown, molecules are required for the pro-hypertrophic, but not for the profibrotic, effects of CCN2 in vivo. We demonstrated that CCN5 inhibited pressure overload-induced cardiac hypertrophy and fibrosis (FIGS. 4 and 5), and prevented cardiac decompensation (FIG. 6). An intriguing hypothesis that a balance between CCN2 and CCN5 determines the state of cardiac hypertrophy and fibrosis may be a subject for future studies.

CCN proteins contain four distinct domains: (i) insulin-like growth factorbinding domain (IGFBD), (ii) von Willebrand factor type-C (vWC), (iii) thrombospondin type-1 (TPS-1), and (iv) C-terminal domain (CT) [22]. CCN5 exceptionally lacks the CT domain that is critical for the hypertrophic activity of CCN2. One intriguing finding of the present study was that deletion of the CT domain in CCN2 renders it a CCN5-like dominant negative molecule. CCN proteins were previously shown to interact with integrins and activate related signaling pathways [29]. However, we observed no changes in FAK, Akt, or ERK activation in AdCCN2- or AdCCN5-infected cardiomyocytes (data not shown). It has been shown that CCN2 binds directly to TGF-β through the vWC domain and facilitates the binding of TGF-β to its receptors [30]. TGF-β-SMAD signaling has been shown to be elevated in CCN2 transgenic mice but inhibited in CCN5 transgenic mice under a pressure overload condition. The CT domain is similar in structure to those found in many growth factors including VEGF, TGF-β, BMP, NGF, and PDGF [31, 32]. It contains a cysteine knot motif of six conserved cysteine residues which is thought to act as a dimerization module. It is possible that CCN5 can bind to TGF-β through its intact vWC domain, but that the lack of the CT domain interferes with the binding of TGF-β to the receptors. Further biochemical analyses are warranted to test this hypothesis.

We showed that TGF-β signaling is modulated by CCN2 and CCN5. Several studies have suggested that TGF-β signaling is involved in cardiac hypertrophy and is fibrosis [33]. Overexpression of TGF-β in TG mice resulted in cardiac hypertrophy characterized by hypertrophic growth of cardiomyocytes and fibrosis [34], whereas the targeted disruption of TGF-β or the blocking of TGF-β using neutralizing antibody inhibited cardiac hypertrophy [35]. SMAD4 has recently been shown to trigger the transition from hypertrophy to apoptosis in cardiomyocytes [36]. The preservation of cardiac function by CCN5 under the condition of pressure overload (FIG. 6) may therefore be a result of the inhibition of the TGF-β-SMAD signaling pathway by CCN5. Cardiac fibrosis is a classical feature of pathological hypertrophy and is characterized by the expansion of the extracellular matrix due to an accumulation of collagen [37]. CCN2 is one of the key pro-fibrotic factors that mediate TGF-β pro-fibrotic activity [5]. Inhibition of cardiac fibrosis by CCN5 may be due to direct inhibition of CCN2 by CCN5. In conclusion, our data demonstrate that CCN5 inhibits cardiac hypertrophy and fibrosis in response to pathological stimuli both in vitro and in vivo. CCN5 appears to exert these anti-hypertrophic and -fibrotic effects by blocking the TGF-β-SMAD signaling pathway. We propose that CCN5 offers a novel therapeutic target for the treatment of cardiac hypertrophy and heart failure.

While the present disclosure has been described with respect to the specific embodiments, it will be apparent to those skilled in the art that various changes and modifications may be made without departing from the spirit and scope of the disclosure as defined in the following claims.

REFERENCE

[1] Hunter J J, Chien K R. Signaling pathways for cardiac hypertrophy and failure. *N Engl Med,* 341(17):1276-83 (1999).

[2] Katz A M. The cardiomyopathy of overload: an unnatural growth response in the hypertrophied heart. *Ann Intern Med,* 121(5):363-71 (1994).

[3] Berenji K, Drazner M H, Rothermel B A, Hill J A. Does load-induced ventricular hypertrophy progress to systolic heart failure? *Am J Physiol Heart Circ Physiol,* 289(1): H8-H16 (2005).

[4] Molkentin J D, Dorn G W, 2nd. Cytoplasmic signaling pathways that regulate cardiac hypertrophy. *Annu Rev Physiol,* 63:391-426 (2001).

[5] Perbal B. CCN proteins: multifunctional signalling regulators. *Lancet,* 363(9402):62-4 (2004).

[6] Bornstein P, Sage E H. Matricellular proteins: extracellular modulators of cell function. *Curr Opin Cell Biol,* 14(5):608-16 (2002).

[7] Chen M M, Lam A, Abraham J A, Schreiner G F, Joly A H. CTGF expression is induced by TGF-beta in cardiac fibroblasts and cardiac myocytes: a potential role in heart fibrosis. *J Mol Cell Cardiol,* 32(10):1805-19 (2000).

[8] Blom I E, Goldschmeding R, Leask A. Gene regulation of connective tissue growth factor: new targets for antifibrotic therapy? *Matrix Biol,* 21(6):473-82 (2002).

[9] Matsui Y, Sadoshima J. Rapid upregulation of CTGF in cardiac myocytes by hypertrophic stimuli: implication for cardiac fibrosis and hypertrophy. *J Mol Cell Cardiol,* 37(2):477-81 (2004).

[10] Ohnishi H, Oka T, Kusachi S, Nakanishi T, Takeda K, Nakahama M, et al. Increased expression of connective tissue growth factor in the infarct zone of experimentally induced myocardial infarction in rats. *J Mol Cell Cardiol,* 30(11):2411-22 (1998).

[11] Yun S H, Shin J O, Lim B K, Kim K L, Gil C O, Kim D K, et al. Change in the cells that express connective tissue growth factor in acute Coxsackievirus-induced myocardial fibrosis in mouse. *Virus Res,* 126(1-2):62-8 (2007).

[12] Hayata N, Fujio Y, Yamamoto Y, Iwakura T, Obana M, Takai M, et al. Connective tissue growth factor induces cardiac hypertrophy through Akt signaling. *Biochem Biophys Res Commun,* 370(2):274-8 (2008).

[13] Panek A N, Posch M G, Alenina N, Ghadge S K, Erdmann B, Popova E, et al. Correction: Connective Tissue Growth Factor Overexpression in Cardiomyocytes Promotes Cardiac Hypertrophy and Protection against Pressure Overload. *PLoS One,* 4(9) (2009).

[14] Zhang R, Averboukh L, Zhu W, Zhang H, Jo H, Dempsey P J, et al. Identification of rCop-1, a new member of the CCN protein family, as a negative regulator for cell transformation. *Mol Cell Biol,* 18(10):6131-41 (1998).

[15] Delmolino L M, Stearns N A, Castellot J J, Jr. COP-1, a member of the CCN family, is a heparin-induced growth arrest specific gene in vascular smooth muscle cells. *J Cell Physiol,* 188(1):45-55 (2001).

[16] Pennica D, Swanson T A, Welsh J W, Roy M A, Lawrence D A, Lee J, et al. WISP genes are members of the connective tissue growth factor family that are up-regulated in wnt-1-transformed cells and aberrantly expressed in human colon tumors. *Proc Natl Acad Sci USA,* 95(25):14717-22 (1998).

[17] Lake A C, Castellot J J, Jr. CCN5 modulates the antiproliferative effect of heparin and regulates cell motility in vascular smooth muscle cells. *Cell Commun Signal,* 1(1):5 (2003).

[18] Lake A C, Bialik A, Walsh K, Castellot 33, Jr, CCN5 is a growth arrest-specific gene that regulates smooth muscle cell proliferation and motility. *Am J Pathol,* 162 (1):219-31 (2003).

[19] Mason H R, Lake A C, Wubben J E, Nowak R A, Castellot 33, Jr. The growth arrest-specific gene CCN5 is deficient in human leiomyomas and inhibits the proliferation and motility of cultured human uterine smooth muscle cells. *Mol Hum Reprod,* 10(3):181-7 (2004).

[20] Frazier K, Williams S, Kothapalli D, Klapper H, Grotendorst G R. Stimulation of fibroblast cell growth, matrix production, and granulation tissue formation by is connective tissue growth factor. *J Invest Dermatol,* 107(3):404-11 (1996).

[21] Kireeva M L, Latinkic B V, Kolesnikova T V, Chen C C, Yang G P, Abler A S, et al. Cyr61 and Fisp12 are both ECM-associated signaling molecules: activities, metabolism, and localization during development. *Exp Cell Res,* 233(1):63-77 (1997).

[22] Brigstock D R. The CCN family: a new stimulus package. *J Endocrinol,* 178(2):169-75 (2003).

[23] Ball D K, Surveyor G A, Diehl J R, Steffen C L, Uzumcu M, Mirando M A, et al. Characterization of 16- to 20-kilodalton (kDa) connective tissue growth factors (CTGFs) and demonstration of proteolytic activity for 38-kDa CTGF in pig uterine luminal flushings. *Biol Reprod,* 59(4):828-35 (1998).

[24] Yang D K, Choi B Y, Lee Y H, Kim Y G, Cho M C, Hong S E, et al. Gene profiling during regression of pressure overload-induced cardiac hypertrophy. *Physiol Genomics,* 30(1):1-7 (2007).

[25] Sadoshima 3, Jahn L, Takahashi T, Kulik T J, Izumo S. Molecular characterization of the stretch-induced adaptation of cultured cardiac cells. An in vitro model of load-induced cardiac hypertrophy. *J Biol Chem,* 267(15): 10551-60 (1992).

[26] Levy D, Garrison R J, Savage D D, Kannel W B, Castelli W P. Prognostic implications of echocardiographically determined left ventricular mass in the Framingham Heart Study. *N Engl J Med,* 322(22):1561-6 (1990).

[27] Katz A M. Cardiomyopathy of overload. A major determinant of prognosis in congestive heart failure. *N Engl J Med,* 322(2):100-10 (1990).

[28] Hardt S E, Sadoshima J. Negative regulators of cardiac hypertrophy. *Cardiovasc Res,* 63(3):500-9 (2004).

[29] Chen Y, Abraham D J, Shi-Wen X, Pearson J D, Black C M, Lyons K M, et al. CCN2 (connective tissue growth factor) promotes fibroblast adhesion to fibronectin. *Mol Biol Cell,* 15(12):5635-46 (2004).

[30] Abreu J G, Ketpura N I, Reversade B, De Robertis E M. Connective-tissue growth factor (CTGF) modulates cell signalling by BMP and TGF-beta. *Nat Cell Biol,* 4(8): 599-604 (2002).

[31] Bork P. The modular architecture of a new family of growth regulators related to connective tissue growth factor. *FEBS Lett,* 327(2):125-30 (1993).

[32] McDonald N Q, Hendrickson W A. A structural superfamily of growth factors containing a cystine knot motif. *Cell,* 73(3):421-4 (1993).

[33] Rosenkranz S. TGF-beta1 and angiotensin networking in cardiac remodeling. *Cardiovasc Res,* 63(3):423-32 (2004).

[34] Rosenkranz S, Flesch M, Amann K, Haeuseler C, Kilter H, Seeland U, et al. Alterations of beta-adrenergic signaling and cardiac hypertrophy in transgenic mice overexpressing TG F-beta (1). *Am J Physiol Heart Circ Physiol,* 283(3): H1253-62 (2002).

[35] Zhao X Y, Zhao L Y, Zheng Q S, Su J L, Guan H, Shang F J, et al. Chymase induces profibrotic response via transforming growth factor-beta 1/Smad activation in rat cardiac fibroblasts. *Mol Cell Biochem,* 310(1-2):159-66 (2008).

[36] Heger 3, Peters S C, Piper H M, Euler G. SMAD-proteins as a molecular switch from hypertrophy to apoptosis induction in adult ventricular cardiomyocytes. *J Cell Physiol,* 220(2):515-23 (2009).

[37] Petrov V V, Fagard R H, Lijnen P J. Stimulation of collagen production by transforming growth factor-beta1 during differentiation of cardiac fibroblasts to myofibroblasts. *Hypertension,* 39(2):258-63 (2002).

---

What is claimed is:

1. A method for reducing cardiac fibrosis in a subject in need thereof, comprising administering to the subject a composition comprising: (a) a therapeutically effective amount of a vector selected from the group consisting of a recombinant adenovirus vector, an adenoassociated virus vector, or a retrovirus vector, wherein the vector comprises a nucleotide sequence encoding a CCN5 protein operably linked to a cardiomyocyte specific promoter; and (b) a pharmaceutically acceptable carrier; wherein said composition is administered into the myocardium of said subject by an injection and CCN5 is expressed in cardiomyocytes in the myocardium of said subject, thereby reducing cardiac fibrosis in the subject with heart failure.

2. The method according to claim 1, wherein the nucleotide sequence encoding CCN5 comprises the nucleotide sequence set forth in SEQ ID NO:1.

3. The method of claim 1, wherein the cardiac fibrosis is induced by pressure overload.

4. The method according to claim 1, wherein CCN5 inhibits TGF-β-SMAD signal pathway.

* * * * *

SEQUENCE LISTING

```
<160> NUMBER OF SEQ ID NOS: 4

<210> SEQ ID NO 1
<211> LENGTH: 756
<212> TYPE: DNA
<213> ORGANISM: Homo sapiens

<400> SEQUENCE: 1 atgagggggca  acccactgat  ccatcttctg  gccatttcct  tcctctgcat  tctctcaatg      60
gtgtatgccc  agctgtgccc  agcaccctgt  gcctgtcctt  ggacaccacc  ccagtgccca     120
ccgggggtac  ccctggtgct  ggatggctgt  ggctgctgtc  gagtgtgtgc  acggaggctg     180
ggggagtcct  gcgaccacct  gcatgtctgc  aaccccagcc  agggcctggt  ttgtcagcct     240
ggggcaggcc  ccagtggccg  tggtgttgtg  tgcctcttcg  aagaggatga  cgggagctgt     300
gaggtgaacg  gccgcaggta  cctggatggg  gagacctta   aacccaattg  cagggttttg     360
tgccgctgtg  atgacggtgg  tttcacctgc  ctgccgctgt  gcagtgagga  tgtgcggctg     420
cccagctggg  actgcccacg  ccccaggaga  atacaggtgc  caggaaggtg  ctgccccgag     480
tgggtgtgtg  accaggcagt  gatgcagccg  gcaatccagc  cctcctcagc  caaggacac     540 caactttctg  cccttgtcac  tcctgcatct  gccgatggcc  cctgtccaaa  ctggagcaca     600
gcctggggcc  cctgctcaac  cacctgtggg  ttgggcatag  ccacccgagt  atccaaccag     660
```

```
aaccgattct gccaactgga gatccagcgt cgcctgtgtc tgtccagacc ctgcctggca    720
tccaggagcc acggctcatg gaacagtgcc ttctag                             756

<210> SEQ ID NO 2
<211> LENGTH: 768
<212> TYPE: DNA
<213> ORGANISM: Homo sapiens

<400> SEQUENCE: 2
atgctcgcct ccgtcgcagg tcccatcagc ctcgccttgg tgctcctcgc cctctgcacc    60
cggcctgcta cgggccagga ctgcagcgcg caatgtcagt gcgcagccga agcagcgccg    120
cactgccccg ccggcgtgag cctggtgctg acggctgcg gctgctgccg gtctgcgcc     180 aagcagctgg gagaactgtg tacggagcgt gaccccgtgcg acccacacaa gggcctcttc    240
tgcgatttcg gctcccccgc caaccgcaag atcggagtgt gcactgccaa agatggtgca    300
ccctgtgtct tcggtgggtc ggtgtaccgc agcggtgagt ccttccaaag cagctgcaaa    360
taccaatgca cttgcctgga tggggccgtg ggctgcgtgc cctgtgcag catggacgtg    420 cgcctgccca gccctgactg ccccttcccg agaagggtca agctgcctgg gaaatgctgc    480
gaggagtggg tgtgtgacga gcccaaggac cgcacagcag ttggccctgc cctagctgcc    540
taccgactgg aagacacatt tggcccagac ccaactatga tgcgagccaa ctgcctggtc    600
cagaccacag agtggagcgc ctgttctaag acctgtggga tgggcatctc caccccgagtt    660 accaatgaca ataccttctg cagacttgag aagcagagtc gcctctgcat ggtcaggccc    720
tgcgaagctg acctggagga aaacattaag aagggagaca tggcgtaa                768

<210> SEQ ID NO 3
<211> LENGTH: 251
<212> TYPE: PRT
<213> ORGANISM: Homo sapiens

<400> SEQUENCE: 3

Met Arg Gly Asn Pro Leu Ile His Leu Leu Ala Ile Ser Phe Leu Cys
 1               5                  10                  15

Ile Leu Ser Met Val Tyr Ala Gln Leu Cys Pro Ala Pro Cys Ala Cys
                20                  25                  30

Pro Trp Thr Pro Pro Gln Cys Pro Pro Gly Val Pro Leu Val Leu Asp
            35                  40                  45

Gly Cys Gly Cys Cys Arg Val Cys Ala Arg Arg Leu Gly Glu Ser Cys
        50                  55                  60

Asp His Leu His Val Cys Asn Pro Ser Gln Gly Leu Val Cys Gln Pro
 65                  70                  75                  80

Gly Ala Gly Pro Ser Gly Arg Gly Val Val Cys Leu Phe Glu Glu Asp
                85                  90                  95

Asp Gly Ser Cys Glu Val Asn Gly Arg Arg Tyr Leu Asp Gly Glu Thr
                100                 105                 110

Phe Lys Pro Asn Cys Arg Val Leu Cys Arg Cys Asp Asp Gly Gly Phe
            115                 120                 125

Thr Cys Leu Pro Leu Cys Ser Glu Asp Val Arg Leu Pro Ser Trp Asp
        130                 135                 140

Cys Pro Arg Pro Arg Arg Ile Gln Val Pro Gly Arg Cys Cys Pro Glu
145                 150                 155                 160

Trp Val Cys Asp Gln Ala Val Met Gln Pro Ala Ile Gln Pro Ser Ser
                165                 170                 175
```

```
Ala Gln Gly His Gln Leu Ser Ala Leu Val Thr Pro Ala Ser Ala Asp
            180                 185                 190

Gly Pro Cys Pro Asn Trp Ser Thr Ala Trp Gly Pro Cys Ser Thr Thr
            195                 200                 205

Cys Gly Leu Gly Ile Ala Thr Arg Val Ser Asn Gln Asn Arg Phe Cys
            210                 215                 220

Gln Leu Glu Ile Gln Arg Arg Leu Cys Leu Ser Arg Pro Cys Leu Ala
225                 230                 235                 240

Ser Arg Ser His Gly Ser Trp Asn Ser Ala Phe
                245                 250

<210> SEQ ID NO 4
<211> LENGTH: 251
<212> TYPE: PRT
<213> ORGANISM: Homo sapiens

<400> SEQUENCE: 4

Met Leu Ala Ser Val Ala Gly Pro Ile Ser Leu Ala Leu Val Leu Leu
1               5                   10                  15

Ala Leu Cys Thr Arg Pro Ala Thr Gly Gln Asp Cys Ser Ala Gln Cys
            20                  25                  30

Gln Cys Ala Ala Glu Ala Ala Pro His Cys Pro Ala Gly Val Ser Leu
            35                  40                  45

Val Leu Asp Gly Cys Gly Cys Cys Arg Val Cys Ala Lys Gln Leu Gly
            50                  55                  60

Glu Leu Cys Thr Glu Arg Asp Pro Cys Asp Pro His Lys Gly Leu Phe
65                  70                  75                  80

Cys Asp Phe Gly Ser Pro Ala Asn Arg Lys Ile Gly Val Cys Thr Ala
            85                  90                  95

Lys Asp Gly Ala Pro Cys Val Phe Gly Gly Ser Val Tyr Arg Ser Gly
            100                 105                 110

Glu Ser Phe Gln Ser Ser Cys Lys Tyr Gln Cys Thr Cys Leu Asp Gly
            115                 120                 125

Ala Val Gly Cys Val Pro Leu Cys Ser Met Asp Val Arg Leu Pro Ser
            130                 135                 140

Pro Asp Cys Pro Phe Pro Arg Arg Val Lys Leu Pro Gly Lys Cys Cys
145                 150                 155                 160

Glu Glu Trp Val Cys Asp Glu Pro Lys Asp Arg Thr Ala Val Gly Pro
            165                 170                 175

Ala Leu Ala Ala Tyr Arg Leu Glu Asp Thr Phe Gly Pro Asp Pro Thr
            180                 185                 190

Met Met Arg Ala Asn Cys Leu Val Gln Thr Thr Glu Trp Ser Ala Cys
            195                 200                 205

Ser Lys Thr Cys Gly Met Gly Ile Ser Thr Arg Val Thr Asn Asp Asn
            210                 215                 220

Thr Phe Cys Arg Leu Glu Lys Gln Ser Arg Leu Cys Met Val Arg Pro
225                 230                 235                 240

Cys Glu Ala Asp Leu Glu Glu Asn Ile Lys Lys
            245                 250
```